United States Patent [19]
Allinson

[11] Patent Number: 4,615,337
[45] Date of Patent: Oct. 7, 1986

[54] PENILE SUPPORT

[76] Inventor: Francis W. Allinson, 53 W. Lewis Ave., Phoenix, Ariz. 85003

[21] Appl. No.: 594,200

[22] Filed: Mar. 28, 1984

Related U.S. Application Data

[63] Continuation-in-part of Ser. No. 542,883, Oct. 10, 1983, abandoned.

[51] Int. Cl.⁴ .............................................. A61F 5/00
[52] U.S. Cl. ...................................................... 128/79
[58] Field of Search .......................................... 128/79

[56] References Cited

U.S. PATENT DOCUMENTS

| | | | |
|---|---|---|---|
| 3,397,689 | 8/1968 | Marcantonio | 128/79 |
| 3,401,687 | 9/1968 | Hood | 128/79 |
| 3,939,827 | 2/1976 | Brunstetter | 128/79 |
| 3,959,254 | 9/1973 | Clark | 128/79 |
| 4,194,502 | 3/1980 | Ecklels | 128/79 |
| 4,262,662 | 4/1981 | Allinson | 128/79 |

FOREIGN PATENT DOCUMENTS 3100491  8/1982  Fed. Rep. of Germany ........ 128/79

Primary Examiner—Dalton L. Truluck

[57] ABSTRACT

This support is used as an aid in male sexual weakness. It is a resilient dorso-lateral clip-on penile support which snaps around the penis and which maintains its shape due to the fact that it is made of a deformable plastic material with a memory. Proximo-distally it is rigid, partly due to the fact that the support is curved laterally, and partly due to the tensile strength of the plastic used in its construction.

The shape of the distal end conforms to the curve of the coronal sulcus and, due to its resilience, it grips here and so displacement distally is prevented. The proximal part of this support is obliquely concave curved so as to more closely come in contact with the tissues in front of the symphysis pubis when in the erect position.

Proximally there are lateral projections which grip the sides of the base of the penis and so prevent dislodgement. The lateral margins of the support are cut away to a greater or lesser degree thus exposing more or less the shaft of the penis. The head of the penis is also completely exposed.

8 Claims, 9 Drawing Figures

U.S. Patent  Oct. 7, 1986  4,615,337
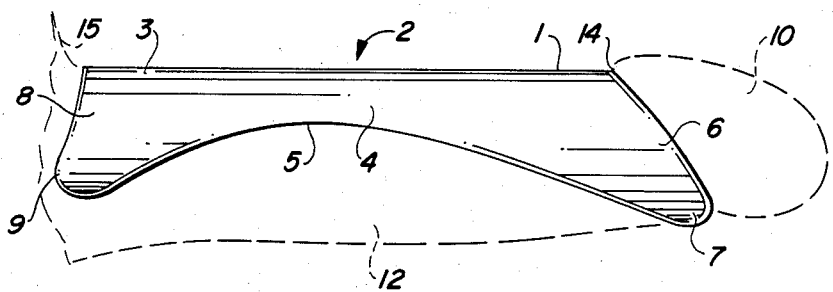
FIG. 1
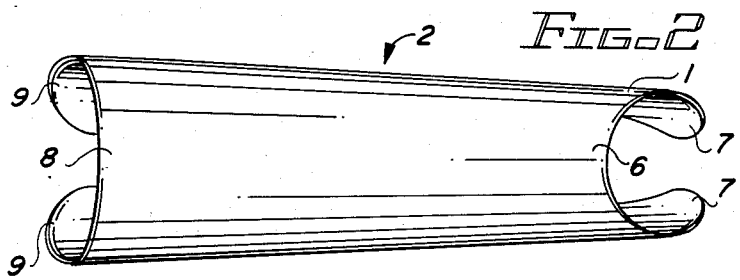
FIG. 2
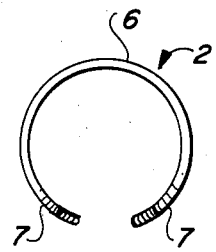
FIG. 8
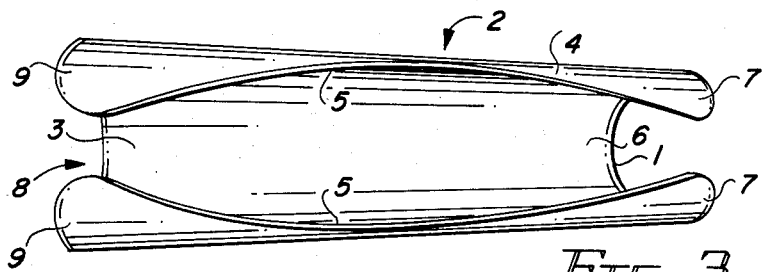
FIG. 3
FIG. 4
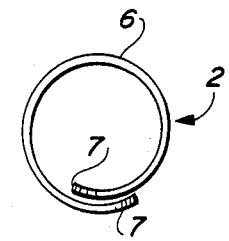
FIG. 9
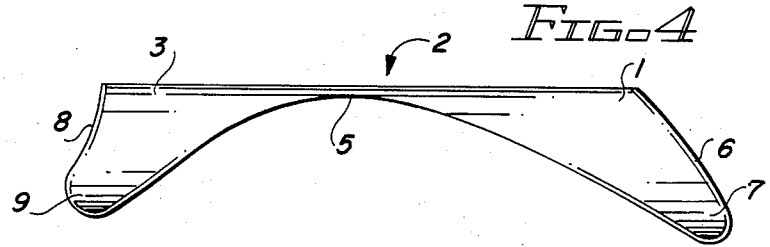
FIG. 5
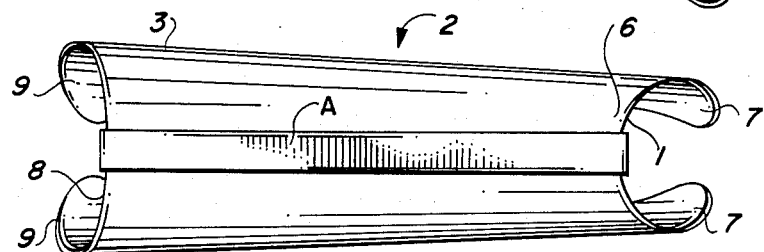
FIG. 6
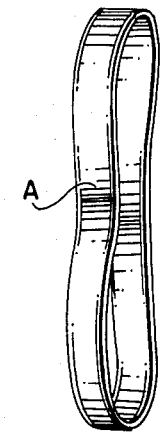
FIG. 7
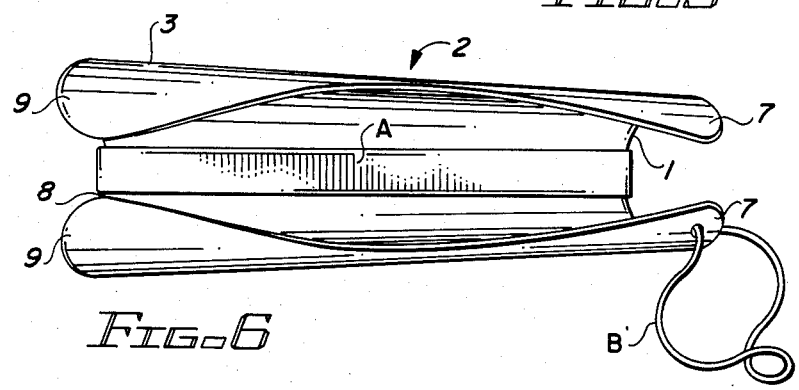

PENILE SUPPORT

This application is a continuation in part of my previous patent application Ser. No. 542,883, filed Oct. 10, 1983, which was abandoned on 2/8/85.

BACKGROUND

1. U.S. Pat. No. 3,397,689 Marcantonio

This has no resemblance to mine as:

This has a sheath member with a longitudinally estending lateral opening, whereas my support is a dorso lateral support, with a ventro-lateral opening, thus exposing the sensitive undersurface of the penis. The distal end is closed, whereas in my support, the distal end is open, thus exposing the glans penis for more intimate contact.

This has a base plate for fixation which is cumbersome and prevents body contact, whereas in my support, there is no base plate, and the proximal end of the support is kept in place by gripping lateral projections of the proximal end of the support, and the end of the support makes direct contact with the user. Thus, in the case of my support, the pubic area of both participants are in contack. This is due to the fact that the proximal end of my support is obliquely concave curved with lateral projections.

2. U.S. Pat. No. 3,401,687 Hood

This has no resemblance to my support as:

The supporting material encompasses the shaft of the penis entirely, whereas in my support, the supporting material encompasses the dorsal and adjacent lateral aspects of the penis. The distal end does not conform to the contour of the coronal sulcus, whereas my support does. This is not a clip-on support, whereas my support is. The proximal end is cut away transversely, whereas in my support this is not so. Here the end is obliquely concave curved with lateral projections.

3. U.S. Pat. No. 3,939,827 Brunstetter

This has no resemblance to may support, as:

The supporting material is ventro-lateral, whereas in my support, the supporting material is dorso lateral. The support is kept in place by a rubber cover fixed either to one or both sides of the supporting material; if fixed to one side only, it could be wrapped around with its other end secured to the wrapped-around portion of the cover. Whereas my support is kept in place by its structure and resiliency. A detachable comparatively narrow rubber band can occasionally be used for added fixation; this in no way resembles the above. Furthermore, this is not a clip-on support whereas mine is. In this support the supporting material conforms to the ventral and lateral portions of the coronal sulcus, whereas in my support the supporting material conforms to the dorsal and adjacent lateral portions of the coronal sulcus. Furthermore the proximal end is cut away transversely, whereas mine is not; it is obliquely concave with curved lateral projections.

4. U.S. Pat. No.3,759,254 Clark

This has no resemblance to my support as:

The supporting material is dorsal and arbitrary, whereas in my support, the supporting material is dorso lateral and constitutes the support itself. A thin walled elongated tubular portion with a closed distal end, whereas in my support, there is no tubular portion and the distal end is open, thus giving full contact of the glans penis with surrounding structures. No mention of conformation with the coronal sulcus. It is therefore hard to see how the penis could be stretched and held in place, whereas in my support, the opposite holds good.

A scrotal bag is included, presumably to fix the proximal portion of the support in position. This is cumbersome and prevents contact of the scrotum with surrounding structures. Whereas in my support, no such scrotal bag is required for fixation. The proximal opening is cut away transversely and laterally and ventrally it is continuous with a thin walled tubular portion. Whereas my support here is obliquely concave curved with lateral projections. There is no dorsal band as in my support; what resembles a band in the drawings is a strip of cartilage.

5. U.S. Pat. No. 4,194,502 Eckles

This has no resemblance to my support as:

The supporting material is ventro lateral, and has an irregular outline, the edges of which could cause damage to the partner, whereas in my support, the supporting material is dorsi lateral and the distal end is protected by the proximal margin of the glans penis adjacent to the coronal sulcus. The lateral side of my support are more or less longitudinal from before backward and therefore cause no damage during use. The anterior end does not conform to the curve of the coronal sulcus and makes fixation impossible. Whereas in my support, the distial end conforms and therefore makes fixation possible when combined with the resilience of the support. The proximal end in no way conforms to the sympathis pubis and has no lateral projections, whereas in my support both these factirs are found. Namely, the proximal end in the support is obliquely concave curved with lateral projections.

6. U.S. Pat. No. 4,262,662 Allinson

Shows a splint device having a distally mounted elastic member. As I was the inventor of the above patent, should I use the above distally mounted member, it would not cause any infringement. This band is unattached; mine is attached. The rest of the splint has no resemblanced to my present one. Amongst other things, it is a sleleton splint and this is not; the proximal end is curved, but in the opposite direction to which mine is curved; and there are here no lateral projections as are present in my present support.

7. German Pat. No. DE 3100491 Bruchle

This has no resemblance to my support as:

It has a tubular sleeve with a slit in the lengthwise direction on the ventral side, whereas my support is a dorso lateral clip-on splint with exposure of the ventro and adjacent lateral surface of the penis. The support is kept in position by gluing the foreskin over the end of the support, whereas the distal end of my support is kept in place by means of its conformation to the coronal sulcus, and its deformability. Furthermore the proximal end is entirely different from my support. Here the proximal end is completely closed ventrally with an opening adjacent to surround the base of the scrotum. Whereas in my support the ventral portion is entirely open and the lateral wings, due to their resiliance and freedon of movement, grip the base of the penis freely. This is not possible in the cse of Bruchle.

When these supports, either separately or collectively, are compared with my suport there are vast differences, chiefly the following:

1. The proximal portion. Where the splint ends proximally in an obleque concave curved proximal end, which will make contact with the tissues covering the symphysis pubis. Lateral projections here, continuous with the lateral part of the main body of the support, grips the base of the penis freely.

2. A central detachable longitudinal rubber band could modify the area of contact between the participants. This is not present in the other supports.

3. My support is a resiliant self-sustaining dorsolateral clip-on support. The others are not.

Other patents were reviewed but they were not considered in contention with the present support. They were as follows:

1. U.S. Pat. No. 3,920,007
2. Russian Patent K 7807A/49X30-589-978
3. German Pat. No. 831.874

SUMMARY OF THE INVENTION

A resiliant self-sustaining clip-on penile support which snaps around the penis and which maintains its shape as it is made of a deformable plastic material with a memory. It is used as an aid in male sexual weakness. The device consists of a distal part, or head piece, a central part, or body, and a proximal part, plus appendages.

The head piece has a distal margin shaped so as to conform to the curve of the coronal sulcus of the penis, and ends vetrally in two distal ventral projections. Due to this and due to its resiliency, the end of the support grips around the coronal sulcus of the penis and thus displacement forwards is prevented during use.

The central part of the support is curved transversely and, due to the tensile strength of the resiliant plastic used, it is held stiff proximo-distally, but is deformable with a memory laterally and here conforms to the transverse curve of the body of the penis. The lateral longitudinal margins of the support are curved longitudinally. The greater the depth of the curve, the narrower will be the body of the support; and the lesser the depth of the curve, the wider will be the body of the support, with corresponding more or less exposure of the adjacent lateral surface of the body of the penis.

The proximal part of the support ends in a proximal margin which is obliquely concave curved. This enables the support to make good contact with the tissues in front of the symphysis pubis; and this will add to the confort and stability of the support when in use and in the erect position. Lateral projections here extend the length of the proximal curve, and due to their resilience, they grip the sides of the base of the penis, and so add to fixation. The appendages are as follows: A centrally placed detachable encompassing longitudinal thin rubber band, which could very in width. This will modify the type of sensation experianced between the participants.

Additional fixation distally is achieved by an elastic member affixed to one of the anterior ventral projections of the head piece, with its distal loop encircling the coronal sulcus of the penis. It is detachable.

Should the support be molded, the edges could be rounded and there could be also different thicknesses in different areas, such as in the body of the support if it is narrow, to prevent bending here.

The support could be covered with a plastic or rubber-like material which could add softness to the surface and would also round the edges. A good resilient plastic for making the support of if Polyethylene with a thickness of 0.0343", namely 21 guage.

DESCRIPTION OF DRAWINGS

The foregoing and further and more specific objects and advantages of the instant invention will become readily apparent to those skilled in the art from the following detailed description of preferred embodiments therefore taken in conjunction with the drawings, in which:

FIG. 1. Shows the lateral view of the penile support, mounted.

FIG. 2. Shows the dorsal view of the penile support.

FIG. 3. Shows the ventral view of the penile support.

FIG. 4. Shows a lateral view of the penile support with more exagerated lateral curve in the central area of the support.

FIG. 5. Shows a centrally placed longitudinal rubber banc (A) in place; shown on dorsal view of penile support depicted in FIG. 4.

FIG. 5. Shows a ventral view of the support depicted in FIG. 5. Also seen is the continuation of the centrally placed dorsal longitudinal rubber band (A). Also depicted in an additional rubber fixational band (B).

FIG. 7. Shows the rubber band depicted in FIGS. 5 & 6A.

FIG. 8. Shows the distal view of the support with the medial margins of the distal projections separated.

FIG. 9. Shows the same view as depicted in FIG. 8, but showing the medial margins of the distal ventral projections overlapping.

DETAILED DESCRIPTION OF THE INVENTION

Turning now to the drawings in which like reference numerals indicate corresponding elements through several views. First discussed is FIG. 1:

This shows a lateral view of a dorso lateral resiliant self-sustaining clip-on penile support which snaps around the penis and which maintains its shape as it is made of a deformable plastic material with a memory. The support has a distal end or head piece (1), a body (2) and a proximal end (3). This figure shows a lateral view of the support mounted on a penis showing glans penis (10) and the body of the penis (12). In the other diagrams shown the support is free and not mounted.

The head piece of the support has a distal end (6) which conforms to the oblique curve of the coronal sulcus of the penis and, due to its resiliance, it grips here and, as it abuts against the corona (14) of the glans penis (10), distal displacement is prevented. The head piece of the support and its distal margin (6) end in two anterior ventral projections (7); they add to the fixation here. In this diagram they do not overlap as the support is clipped on the penis.

Turning now to the body (2) of the support. This shows the lateral portion (4) on one side only. The lateral margin (5) of the support is seen; it is curved longitudinally, and the degree of the curve varies: the greater the degree, the narrower will be the central part (2) of the support and the greater the exposure of the adjacent lateral surface of the body of the penis (12). The lesser the degree of the curve of the lateral margin (5), the greater the width of the central part (2) of the support, and the lesser the exposure of the lateral surface of the penis (12). The proximal end (3) of the support is shown ending in an obliquely concave curved end (8) with lateral projections (9). This enables the proximal end of the support (3) to make good contact with the tissues in front of the symphysis pubis (15) during use.

The medial ends of the distal ventral projections (7) will generally not overlap when the support is clipped onto the penis, as shown in FIGS. 1 & 8, but will overlap when the support is not in use due to the resilience of the material used in its construction. FIGS. 2,3,4,& 5 do not show this overlap in order to more clearly show the construction of the distal end of the support (1) but this overlap is shown in FIG. 9. The body surface (15) is shown.

FIG. 2:

This shows a dorsal view of the support, with its distal end or head piece (1) with its curved distal margin (6) and the two distal ventral projections (7). The body (2) of the support and the proximal end (3) with its obliquely curved margin (8) and its posterior lateral projections (9) which grip the sides of the base of the penis, and so prevent dislodgement here due to its resiliance.

FIG. 3:

This shows a ventral view of the support. The ventral surface of the distal ventral projections (7) are seen. Also seen is a small central section of the distal curved margin (6) of the support. The lateral part (4) of the body (2) of the support is here shown as curved in. This is due to the resilience of the support. The longitudinally curved lateral margins (5) of the support are seen. The proximal lateral projections (9) are shown turned in due to the resilience of the support. The proximal curved margin (8) is also seen and clearly demonstrates the obliquity.

FIGS. 4,5 and 6:

Using like reference numbers as seen in FIG. 1:- these show lateral, dorsal and ventral views of the support, which only differs from the support shown above FIG. 1 by having a more pronounced, deeper, concave, curved lateral margin (5).

FIG. 4:

This shows a lateral view of the support; the increased curve of the lateral margin (5) is clearly seen.

FIG. 5:

This shows a dorsal view of the support depicting a detachable thin rubber band (A) which may be of different widths and which encircles the support proximodistally in the mid line, the outside portion only of the rubber band being visible. This rubber band is used to improve surface contact between participants.

FIG. 6:

This depicts a ventral view of the support depicting the inside portion of the thin rubber band (A) the exterior portion already shown in FIG. 5. It also shows a thin and small detachable rubber band (B) which has been looped through a perforation in one of the two anterior ventral projections (7). The free loop encircles the coronal sulcus for additional fixation if and when required.

FIG. 7:

This shows separately the encircling thin rubber band (A) described in FIGS. 5 and 6.

FIG. 8:

This shows an anterior view of the support shown in FIG. 1. The curved distalend (6) of the head piece (1) is shown and ends ventrally in the medial margins of the distal anterior ventral projections (7) of the head piece (1). They are here shown as separated, as usually occurs when the support is in use.

FIG. 9:

This is a similar view of the support as shown in FIG. 8. Here the medial margins of the distal ventral projections (7) overlap, as occurs when the support is not in use, or the head piece is comparatively large. This is due to the resilience of the support.

All supports are made of different sizes so as to fit the user.

Having fully described and disclosed this present invention and alternately preferred embodiment thereof in such clear and concice terms as to enable those skilled in the art to understand and practice the same, what I claim is:

1. A clip-on, resiliant, self-sustaining, penile support comprising:
   a transversly curved resiliant distal portion for extending around and gripping a forward portion of the penis proximal to the corona of the glans penis;
   a transversly curved resiliant proximal portion for extending around and gripping a rear portion of the said penis; and
   a longitudinal transversly curved support portion contiguous with and intermediate with proximal and distal portions and having longitudinally curved sides for exposing an under surface and adjacent lateral surface of said penis.

2. The clip-on, resiliant, self-sustaining, penile support of claim 1 further comprising first and second lateral projections contiguous with said proximal portion.

3. The clip-on, resiliant, self-sustaining, penile support of claim 2 further comprising first and second anterior ventral projections contiguous with opposite sies of said distal portion.

4. The clip-on, resiliant, self-sustaining, penile support of claim 1 further comprising first rubber band means for longitudinally encircling said penile support.

5. The clip-on, resiliant, self-sustaining, penile support of claim 4 further comprising second rubber band means coupled to one of the first and second anterior ventral projections.

6. The clip-on, resiliant, self-sustaining, penile support of claim 1 wherein the proximal portion includes an obliquely concave proximal end.

7. The clip-on, resiliant, self-sustaining, penile support of claim 1 where the distal portion includes an obliquely concave distal end.

8. The clip-on, resiliant, self-sustaining, penile support of claim 1 wherein the degree of the curve of the longitudinally curved sides is variable.

* * * * *